United States Patent [19]

Kruppa

[11] Patent Number: 4,474,749

[45] Date of Patent: Oct. 2, 1984

[54] ANTICARIOGENETIC CHEWING GUM

[76] Inventor: Winfried Kruppa, Vilstalstrasse 88, D-8451 Kümmersbruck 1, Fed. Rep. of Germany

[21] Appl. No.: 482,897

[22] Filed: Apr. 7, 1983

[30] Foreign Application Priority Data

Apr. 8, 1982 [DE] Fed. Rep. of Germany ....... 3213284

[51] Int. Cl.³ .............................................. A23G 3/30
[52] U.S. Cl. .......................................... 424/48; 426/3; 426/74; 424/49; 424/52
[58] Field of Search ....................................... 426/3–6, 426/74; 424/48, 49, 54, 199, 52

[56] References Cited

U.S. PATENT DOCUMENTS

| | | | |
|---|---|---|---|
| 3,932,608 | 1/1976 | Anderson et al. | 424/48 |
| 4,233,288 | 11/1980 | Cornell | 424/48 |
| 4,284,650 | 8/1981 | Goupil | 426/5 |
| 4,384,004 | 5/1983 | Cea et al. | 426/5 |

Primary Examiner—Jeanette Hunter

[57] ABSTRACT

Anticariogenetic chewing gum containing a known chewing gum base, sodium fluoride, calcium citrate, tricalcium-bis-orthophosphate, and additives as desired, and as an essential ingredient, a prolamin (Zein G-200) which is applied to the sodium fluoride during processing of the gum.

4 Claims, No Drawings

ANTICARIOGENETIC CHEWING GUM

BACKGROUND OF THE INVENTION

The present invention relates to an anticariogenic chewing gum containing a chewing gum base known in itself, sodium fluoride, calcium citrate, tricalcium-bis-orthophosphate and additives, and also to a method for its manufacture.

98% of all Germans have been suffering since childhood from dental caries. It is known to use fluorine and fluorides for the prevention of tooth decay. Also, mineral substances are administered, especially calcium and phosphates. These can be used in preparing toothpastes, mouthwashes, tablets, gels and coatings.

Experience, however, has shown that satisfactory results are not obtainable by these methods of application, especially because they cannot be applied regularly.

On the other hand, chewing gums are also known. These contain as their principal component chicle or other base substances such as butadiene-styrene copolymers, gutta percha, polyethylene, polyvinyl esters etc., with which additives can be combined, particularly in accordance with the Chewing Gum Decree of Dec. 19, 1959 (BGBl. I p. 754) and Amendment Decree of Aug. 21, 1964 (BGBl. I p. 703).

One object of the present invention is to avoid the disadvantages associated with the above-described application of fluorine and mineral substances, and especially to create a possibility for applying fluorine and mineral substances over long periods of time without harmful side effects.

BRIEF DESCRIPTION OF THE INVENTION

This object is achieved in accordance with the invention by the fact that the anticariogenic chewing gum of the kind described above contains zein G-200.

In accordance with the invention, the sodium fluoride granules contained in the chewing gum are encased in 0.0004 to 0.001 weight-percent of zein G-200.

In a preferred embodiment, the anticariogenic chewing gum of the invention consists of:
  0.04 to 0.05 wt. % of sodium fluoride
  0.0004 to 0.001 wt. % of zein G-200
  12 wt. % of calcium citrate,
  4 wt. % of tricalcium-bis-orthophosphate, and chewing gum base to make 100%.

The process of the invention for the preparation of the anticariogenic chewing gum is characterized by the fact that first calcium citrate and tricalcium-bis-orthophosphate are mixed with the base by kneading, and then, by means of a homgenizer, the sodium fluoride granules encased in zein G-200 are incorporated into this mixture in the form of a homogeneous emulsion in an acid medium together with the customary additives.

Zein G-200 is a protein product (a prolamin) which is obtained from the gluten of corn grain by extraction with dilute ethyl alcohol. It is a copolymer of amino acids, with a molecular weight of about 25,000, which is soluble in aqueous alcohols, in glycols and glycol ethers and in alkalies, but not in water. A more precise definition is to be found in the "Lexikon der Hilfsstoffe" by H. P. Fidler, 1981 edition, vol. 2, p. 1020, Editio Cantor Verlag, Aulendorf. This more precise definition is quoted, in English translation, as follows:

Zein G-200 is a protein product (prolamin) which is obtained by extraction with dilute ethyl alcohol from the gluten of corn grain. It is a copolymer of amino acids with a molecular weight of approximately 25,000, which is soluble in aqueous alcohols, in glycols and glycol ethers and in alkalies, but not in water. Zein G-200 is a light cream-colored, amorphous powder for which the following characteristics are given: $D.^{25}$ 1.25, melting point (decomposition) 180°–200°, isoelectric point 6.2, dielectric constant 4.9–5.0. It consists to at least 98% of protein and contains a maximum of 8% of volatile components. Composition (in %, the figures given between parentheses indicate moles per mole of zein [molecular weight 25,000]): glutamine 21.4 (43), glutamic acid 1.5 (3), leucine 19.3 (44), isoleucine 6.2 (14), proline 9.0 (24), alanine 8.3 (30), phenylalanine 6.8 (12), tyrosine 5.1 (8), threonine 2.7 (7), valine 3.1 (8), serine 5.7 (17), asparagine 4.5 (10), methionine 2.0 (4), arginine 1.8 (3), histidine 1.1 (2), cystine 0.8 (1), glycine 0.7 (3). Reactive groups: amino-1, amide-53, hydroxyl-24, carboxyl-4 and phenol-8.

BRIEF DESCRIPTION OF A PREFERRED EMBODIMENT

An example of the invention is given herewith, which represents its best embodiment:

By the method described above, 1.25 g of chewing gum (=100% by weight) was prepared. First 0.15 g of calcium citrate and 0.05 g of tricalcium-bis-orthophosphate were mixed with the chewing gum base by kneading. Then 553 mg of sodium fluoride granules were microcoated with 5 to 6 mg of zein G-200 and added in the form of a homogeneous emulsion in an acid medium together with the customary additives, by means of a homogenizer.

The microcoating of sodium fluoride with zein G-200 is performed by a process of turbulent countercurrent spraying, also known as fluid bed granulation or the turbulent flow process. The sodium fluoride is injected from below into a closed pot. A solution of about 2.5% zein in ethyl alcohol is injected from the top and sides through nozzles. By then blowing hot air into the kettle, the ethyl alchol is evaporated in the turbulent flow and exhausted. It is in the drying that the microcoating takes place.

When the zein-coated sodium fluoride together with the ethereal oils is incorporated into the base mixture, the adjustment of the pH is performed preferably with citric acid. To prevent the microcoating on the sodium fluoride from dissolving during manufacture while it is being mixed with the rest of the components, the zein-coated sodium fluoride is placed in an aqueous solution adjusted with citric acid to pH 1.5 to 1.8, and allowed to stand for several hours at a temperature of about 25° to 30°. During this time the acid deposits itself in the outermost layer of the zein. Then, by means of an emulsifier, the sodium fluoride thus treated is mixed with the ethereal oils to form an emulsion. The ethereal oil lays itself like a coating about the pretreated sodium fluoride granules so that an acid buffer forms between the ethereal oil and the zein coating, and persists while the sodium fluoride is being incorporated into the chewing gum composition, and it dissolves while the gum is being chewed in the mouth due to the conditions prevailing therein, especially the presence of enzymes and the mainly basic medium of the rest of the components, so that the sodium fluoride is released in the mouth.

With the anticariogenic chewing gum of the invention, fluorine is prevented from depositing itself in the bone substance. The zein-coated sodium fluoride granules can be dissolved only in the oral cavity. The pH of the mouth normally amounts to 7 to 7.5. When the anticariogenic gum of the invention is chewed, the pH increases from 8 to 9. If undissolved zein-coated sodium fluoride granules enter the stomach, they are not dissolved at the pH of 1 prevailing therein, and they are excreted undissolved from the body.

The anticariogenic chewing gum of the invention, manufactured preferably in the form of dragees, is enjoyed by persons of all ages, but especially by children who should be given special attention for the prevention and reduction of caries.

Physiologically, fluorine is a trace element. The amount consumed daily with foods amounts to approximately 0.3 mg. The same is true of calcium and phosphate. These active substances can produce a remedial effect only when they are consumed in larger amounts. The required amounts of such active substances or medicaments can be administered by means of the anticariogenic chewing gum of the invention.

I claim:

1. In an anticariogenic chewing gum comprising a chewing gum base, sodium fluoride, calcium citrate, tricalcium-bis-orthophosphate and additives, the improvement wherein said sodium fluoride is microcoated by zein G-200.

2. An anticariogenic chewing gum comprising a chewing gum base, sodium fluoride, calcium citrate, tricalcium-bis-orthophosphate, additives, and zein G-200, produced by the process comprising first mixing calcium citrate and tri-calcium-bis-orthophosphate with said base to form a base mixture, enveloping the sodium fluoride with zein G-200 by spraying said zein G-200 on said sodium floride to form a microcoating thereon subjecting said thus coated sodium fluoride to an acid aqueous solution and maintaining it therein for a time sufficient for the acid in said solution to deposit on the outermost layer of said zein, then processing the thus-treated sodium fluoride with an emulsifying agent to form an emulsion, and lastly, incorporating said emulsion into the base mixture by means of a homogenizer.

3. Anticariogenic gum of claim 2 wherein said sodium fluoride is enveloped in from about 0.0004 to 0.001 per cent by weight of zein G-200.

4. Anticariogenic chewing gum of claim 2 or claim 3, wherein the sodium fluoride microcoated by zein G-200 is subjected to an aqueous solution adjusted with citric acid to pH from about 1.5 to 1.8 and maintained therein at a temperature of from about 25° C. to 30° C. for a time sufficient for the acid in said solution to deposit on the outermost layer of said zein.

* * * * *